US00PP09202P

United States Patent [19]

Hoff

[11] Patent Number: Plant 9,202

[45] Date of Patent: Jul. 18, 1995

[54] VARIETY OF LILIUM NAMED 'HOLEBT'

[75] Inventor: Petrus M. M. Hoff, Steenbergen, Netherlands

[73] Assignee: Hoffgaarde B.V., Netherlands

[21] Appl. No.: 312,212

[22] Filed: Sep. 26, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

*Attorney, Agent, or Firm*—Webb Ziesenheim Bruening Logsdon Orkin & Hanson

[57] ABSTRACT

A new and distinct cultivar of lily plant named Holebt, particularly characterized by ivory-blushed-with-magenta upper surface and ivory lower surface of the flowers, height of about 70–80 cm, pedicel of 10–12 cm in length with 2–4 flowers, and capable of producing stems and flowers for cut-flower production.

1 Drawing Sheet

BACKGROUND OF THE INVENTION

The present invention comprises a new and distinct cultivar of lily, botanically known as Lilium asiatic and hereinafter referred to by the cultivar named Holebt.

The new cultivar is a product of a planned breeding program which had the objectives of creating new lily cultivars with the capacity to produce stems and flowers for cut-flower production.

The new cultivar was orginated from a hybridization made by the inventor Messr. Petrus Mattheus Maria Hoff in a controlled breeding program at Hoffgaarde B.V., Franseweg 9, 4651 PV Steenbergen, The Netherlands in 1989. The female and male parents were seedlings originated by Applicant, which were proprietary and maintained by Applicant for breeding purposes.

The new cultivar was discovered and selected as one flowering plant within the progeny of the stated cross by the inventor on May 15, 1991 in a controlled environment in Steenbergen.

The first act of asexual reproduction of the new cultivar was accomplished by the inventor when scales were taken from the initial selection on Dec. 4, 1991 in a controlled environment in Steenbergen.

Horticultural examination of clonal specimens initiated Mar. 22, 1992 has demonstrated that the combination of characteristics as herein disclosed for the new cultivar are firmly fixed and are retained through successive generations of asexual reproduction.

The new cultivar has not been observed under all possible environmental conditions. The phenotype may vary significantly with variations in environment such as temperature, light, intensity, and day length. The following observations, measurements, and comparisons describe plants grown in Steenbergen under greenhouse conditions which approximate those generally used in commercial practice.

The following traits have been repeatedly observed and are determined to be basic characteristics of the new cultivar which in combination distinguish this lily as a new and distinct cultivar.

(1) Flower color having an interesting ivory-brushed-with-magenta character with tepals having an essentially ivory ground color centrally with progressively more intense magenta blush with progressive proximity to the apex of each tepal.

(2) Plant height of 70–80 cm.

(3) Pedicel 10–12 cm in length with 2–4 flowers.

DESCRIPTION OF THE DRAWING

The accompanying color photographic drawing shows typically flower characteristics of the new cultivar, with colors being as true as possible with illustrations of this type.

DESCRIPTION OF THE NEW PLANT

In the following description, color references are made to the Royal Horticultural Society Colour Chart. The color values were determined at Steenbergen on Mar. 22, 1992.

THE PLANT

Classification:

*Botanic.*—*Lilium asiatic.*

*Commercial.*—Hybrid asiatic lily for cut-flower production.

Form: Single upright stem from each bulb

*Height.*—70–80 cm.

*Growth habit.*—Upright, erect, some tendency for leaf burning with extreme sunlight.

Stem:

*Diameter.*—1.2 cm average.

*Form.*—Rounded.

*Color.*—Green Group 137C.

Foliage:

*Quantity.*—70–85 leaves.

*Size of leaf.*—12 cm maximum; breadth up to 1.6 cm.

*Shape of leaf.*—Elliptic.

*Texture of leaf.*—Smooth.

*Color.*—Green Group 137A.

Bulbs:

*Size.*—10–12 cm in circumference.

*Color.*—White.

THE BUD

Form: Oblong, pointed ends.

Size: 8 cm in length.

Color: Yellow-Green Group 145B.

Shape: Oblancealate (UPOV Type V).

THE FLOWER

Blooming habit: About 75 days after planting.

Size: 14 cm in diameter.

Borne: Compound umbellate (UPOV Type IV).

Tepalage:

*Number of tepals.*—6.

*Arrangement.*—Hexagonal.

*Appearance.*—Magenta color lies like paint on the otherwise ivory surface.

*Color.*—Top: Inner area is White Group 155A and outer area starting at apex and extending inward is Red-Purple Group 57A; magenta color dulls with age to Red-Purple Group 51A and 51B. Bottom: Ivory colored White Group 155A.

*Spotting.*—Very little spotting; spots that do occur are small (0.7 mm) and located from throat outward to approximately halfway; spots are Greyed-Orange Group 166A.

*Surfrace.*—Smooth, inner tepals tend not to overlap outer tepals.

*Texture.*—Smooth, no papillae.

Pedicel:

*Length.*—6 cm.

*Form.*—Upright.

*Shape.*—Rounded.

Nectaries:

*Color.*—Yellow Group 4A.

*Size.*—Large, up to 2 cm in length.

Disease resistance: No unusual problems have been observed.

Fragrance: None.

Lasting quality: 12 days in water at room conditions after cutting.

REPRODUCTIVE ORGANS

Stamens:

*Number.*—6.

*Length.*—6 cm.

Pistils:

*Number.*—1.

*Stigma color.*—Greyed-Orange Group 166A.

Ovaries:

*Color.*—Yellow-Green Group 145A.

I claim:

1. A new and distinct variety of lily plant substantially as shown and described.

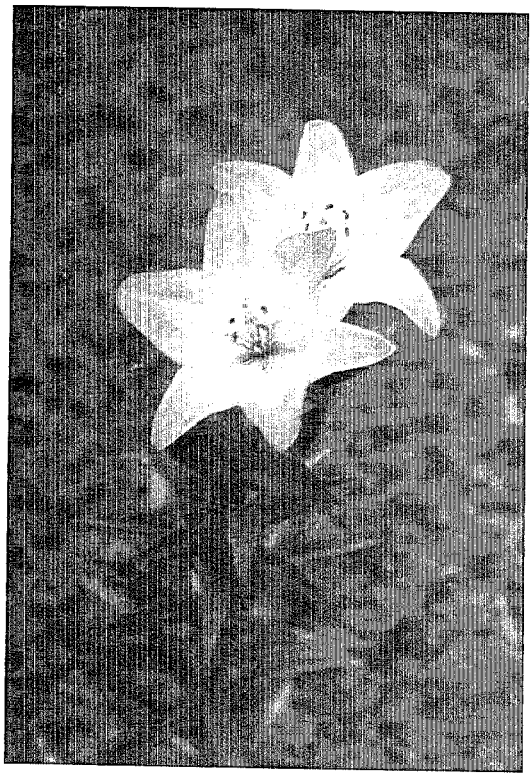

* * * * *